United States Patent
Stavely et al.

(10) Patent No.: US 7,259,785 B2
(45) Date of Patent: Aug. 21, 2007

(54) DIGITAL IMAGING METHOD AND APPARATUS USING EYE-TRACKING CONTROL

(75) Inventors: Donald J. Stavely, Windsor, CO (US); Kenneth Jay Hall, Windsor, CO (US); Amy E. Battles, Windsor, CO (US); Sarah Jean Barrios, Fort Collins, CO (US); Robert E. Sobol, Fort Collins, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 728 days.

(21) Appl. No.: 10/425,292

(22) Filed: Apr. 28, 2003

(65) Prior Publication Data

US 2004/0212712 A1 Oct. 28, 2004

(51) Int. Cl.
*H04N 5/76* (2006.01)
(52) U.S. Cl. .............................. 348/231.3; 348/333.03
(58) Field of Classification Search ............ 348/231.3, 348/333.03, 333.05; 396/51
See application file for complete search history.

(56) References Cited

U.S. PATENT DOCUMENTS

| | | | |
|---|---|---|---|
| 5,253,008 A * | 10/1993 | Konishi et al. ............... 396/51 |
| 5,422,700 A | 6/1995 | Suda et al. | |
| 5,745,174 A | 4/1998 | Nakano | |
| 5,757,428 A | 5/1998 | Takei | |
| 5,990,954 A * | 11/1999 | Kobayashi et al. .... 348/333.03 |
| 6,035,054 A | 3/2000 | Odaka et al. | |
| 6,091,899 A | 7/2000 | Konishi et al. | |
| 6,097,894 A | 8/2000 | Suda | |
| 6,229,959 B1 | 5/2001 | Suda et al. | |
| 6,394,602 B1 | 5/2002 | Morrison et al. | |
| 6,424,376 B1 * | 7/2002 | Hirasawa ................ 348/333.03 |
| 6,507,702 B2 | 1/2003 | Ohtani | |
| 6,522,360 B1 * | 2/2003 | Miyawaki et al. ...... 348/333.03 |
| 6,906,751 B1 * | 6/2005 | Norita et al. ........... 348/333.01 |
| 7,034,878 B2 * | 4/2006 | Matsushima ........... 348/333.03 |
| 7,046,924 B2 * | 5/2006 | Miller et al. .................. 396/51 |
| 2003/0067551 A1 * | 4/2003 | Venturino et al. .......... 348/364 |

FOREIGN PATENT DOCUMENTS

| JP | 05-005925 | 1/1993 |
|---|---|---|
| JP | 05-164958 | 6/1993 |
| JP | 08-307739 | 11/1996 |

OTHER PUBLICATIONS

Canon EOS ELAN 7E 35mm SLR Camera, Epinions.com, http://www.epinions.com/content_61084176004, printed Mar. 14, 2003, 3 pages.
User Report: Canon EOS Elan 7, PHOTOgraphic Magazine, http://www.photographic.com/showarchives.cgi?35, printed Mar. 14, 2003, 2 pages.
Canon Elan 7E 35mm SLR Camera Outfit w/Canon EF 28-90mm f/4-5.6 USM Lens, Canon (Cameras) Outpost.com, http://www.outpost.com/product/2951725/, printed Mar. 14, 2003, 4 pages.
Lens Store, Canon EOS ELAN 7E 35mm SLR Camera Kit w/28-90mm Lens, CamerasAndCameras.com, http://www.camerasandcameras.com/1/Lens/Canon_EOS_ELAN_7E_35mm_SLR_Camera . . . , printed Mar. 14, 2003, 2 pages.

* cited by examiner

*Primary Examiner*—Vivek Srivastava
*Assistant Examiner*—Gevell Selby

(57) ABSTRACT

A digital imaging device detects or tracks a user's direction of gaze. The detected direction of gaze may be used to set one or more functions in the digital imaging device, and the history of the user's direction of gaze may be stored with a captured digital image for later use by an automatic image post-processing apparatus.

22 Claims, 11 Drawing Sheets

DIGITAL IMAGING METHOD AND APPARATUS USING EYE-TRACKING CONTROL

RELATED APPLICATIONS

The instant application is related to "Method and Apparatus for Automatic Post-Processing of a Digital Image," Hewlett-Packard Company U.S. Ser. No. 10/425,293, which was filed on the same day.

FIELD OF THE INVENTION

The present invention relates generally to digital imaging devices such as digital cameras and more specifically to user interfaces for such devices.

BACKGROUND OF THE INVENTION

Autofocus, auto exposure, and auto color balance have become standard features on both film and digital cameras. Some cameras control autofocus using an eye-tracking user interface. Such a camera determines at which part of a scene the user is looking by sensing the direction in which the user's eyes are pointed. The autofocus distance may be set according to the part of the scene at which the user is gazing.

In a camera employing the simplest form of eye tracking, the autofocus distance is based on where the user is looking at the instant S1 (the intermediate position of the two-position shutter release button) is activated. More sophisticated cameras are capable of tracking the user's direction of gaze throughout the entire picture composition process, updating the autofocus setting accordingly in response to the user looking at various portions of the scene. However, even such sophisticated cameras do not include other useful features that can be provided through use of eye-tracking control.

It is thus apparent that there is a need in the art for an improved digital imaging method and apparatus using eye-tracking control.

SUMMARY OF THE INVENTION

A method for controlling the operation of a digital imaging device using eye-tracking control is provided. An apparatus is also provided for carrying out the method.

Other aspects and advantages of the present invention will become apparent from the following detailed description, taken in conjunction with the accompanying drawings, illustrating by way of example the principles of the invention.

DETAILED DESCRIPTION OF THE INVENTION

More effective use may be made of eye-tracking control by using it to control other parameters in a digital imaging device such exposure and color balance, for example, in addition to autofocus. In a digital imaging device such as a digital camera, a preview of how a scene would appear if captured in a digital image may be shown to provide a user with immediate feedback. As the user looks at various parts of the scene, the preview may be updated accordingly. The adjustment of parameters such as exposure and color balance by eye-tracking control may also be applied to a localized area within the scene (the sky only, for example), and a preview of the localized area may be shown. In such an embodiment, eye-tracking control directs a localized process simulating a form of "dodge-and-burn" effect.

Storing a history of the user's direction of gaze throughout the image composition process provides other advantages. First, parameters such as autofocus, exposure, and color balance may be adjusted based on a weighting of multiple "dwell locations" or gaze fixation points (portions of the scene on which the user's gaze lingers during the composition process). For example, more recent dwell locations having longer associated dwell times may be weighted more heavily than other dwell locations. Secondly, storing along with a digital image as metadata a single dwell location or a richer history of dwell locations with their associated dwell times makes possible still other capabilities. For example, digital image processing system may post-process the image automatically based on the metadata accompanying the image. For example, the image may be cropped automatically according to the single dwell location, or a weighting of multiple dwell locations may be used to alter the image intelligently without the need for user involvement.

These and other aspects of the invention will be explained more fully in the balance of this detailed description.

Figure 1A:
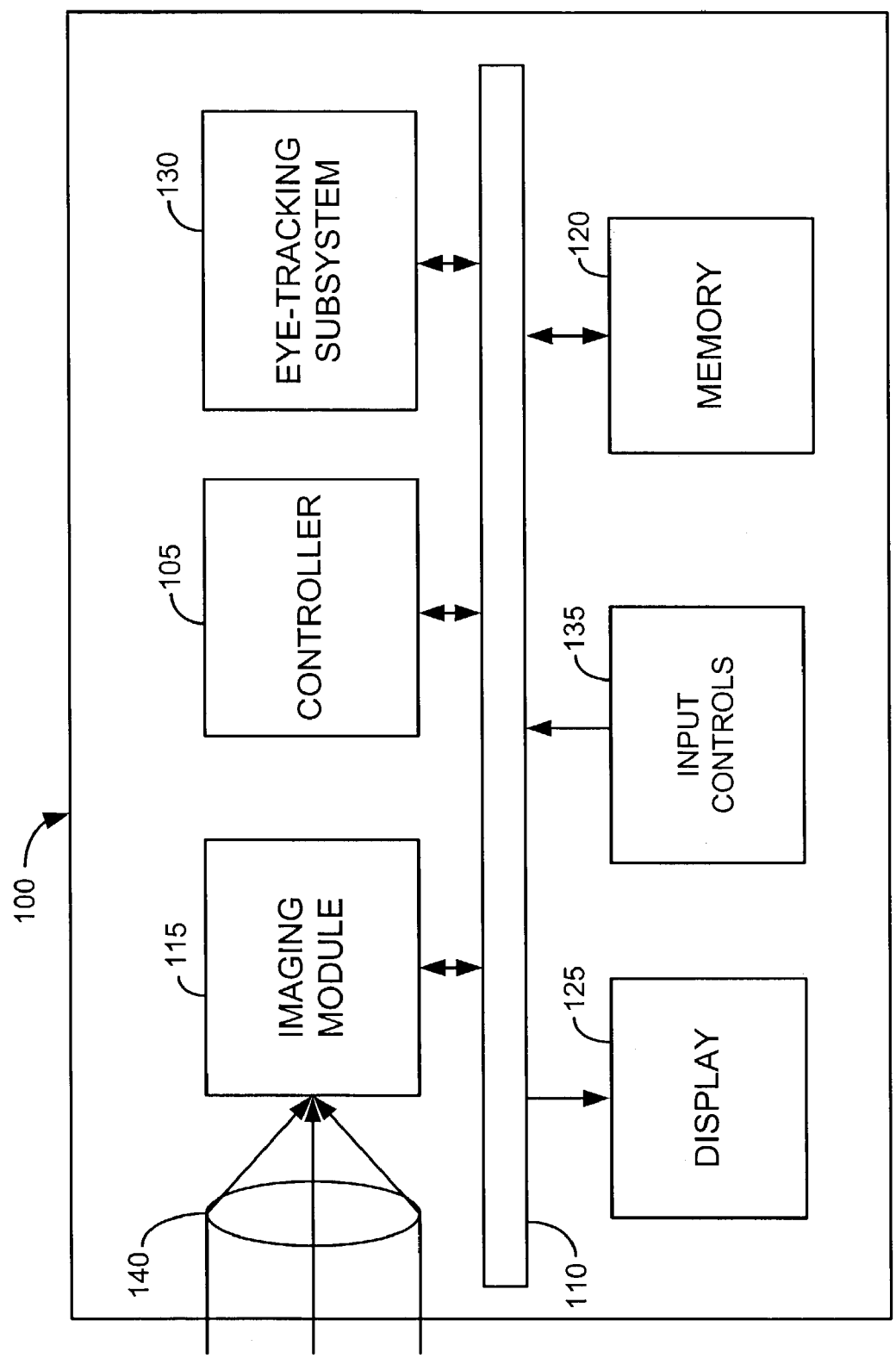
FIG. 1A is a functional block diagram of a digital imaging device in accordance with an illustrative embodiment of the invention.

FIG. 1A is a functional block diagram of a digital imaging device 100 in accordance with an illustrative embodiment of the invention. In FIG. 1A, controller 105 communicates over data bus 110 with imaging module 115, memory 120, display 125, eye-tracking subsystem 130, and input controls 135. Controller 105 may, for example, comprise a microprocessor or microcontroller. Optical system 140 produces optical images that are converted to digital images by imaging module 115. Imaging module 115 may comprise an array of photosensors based on charge-coupled-device (CCD) or CMOS technology, an analog-to-digital converter (A/D), a gain control, and a digital signal processor (DSP) (not shown in FIG. 1A). Input controls 135 may comprise a shutter release button having an intermediate position ("S1") and an image capture position ("S2"), navigational buttons, a menu button, and an "OK" button (not shown in FIG. 1A). Digital imaging device 100 may be a digital camera, digital camcorder, or any other similar device that is capable of converting optical images to digital images.

Figure 1B:
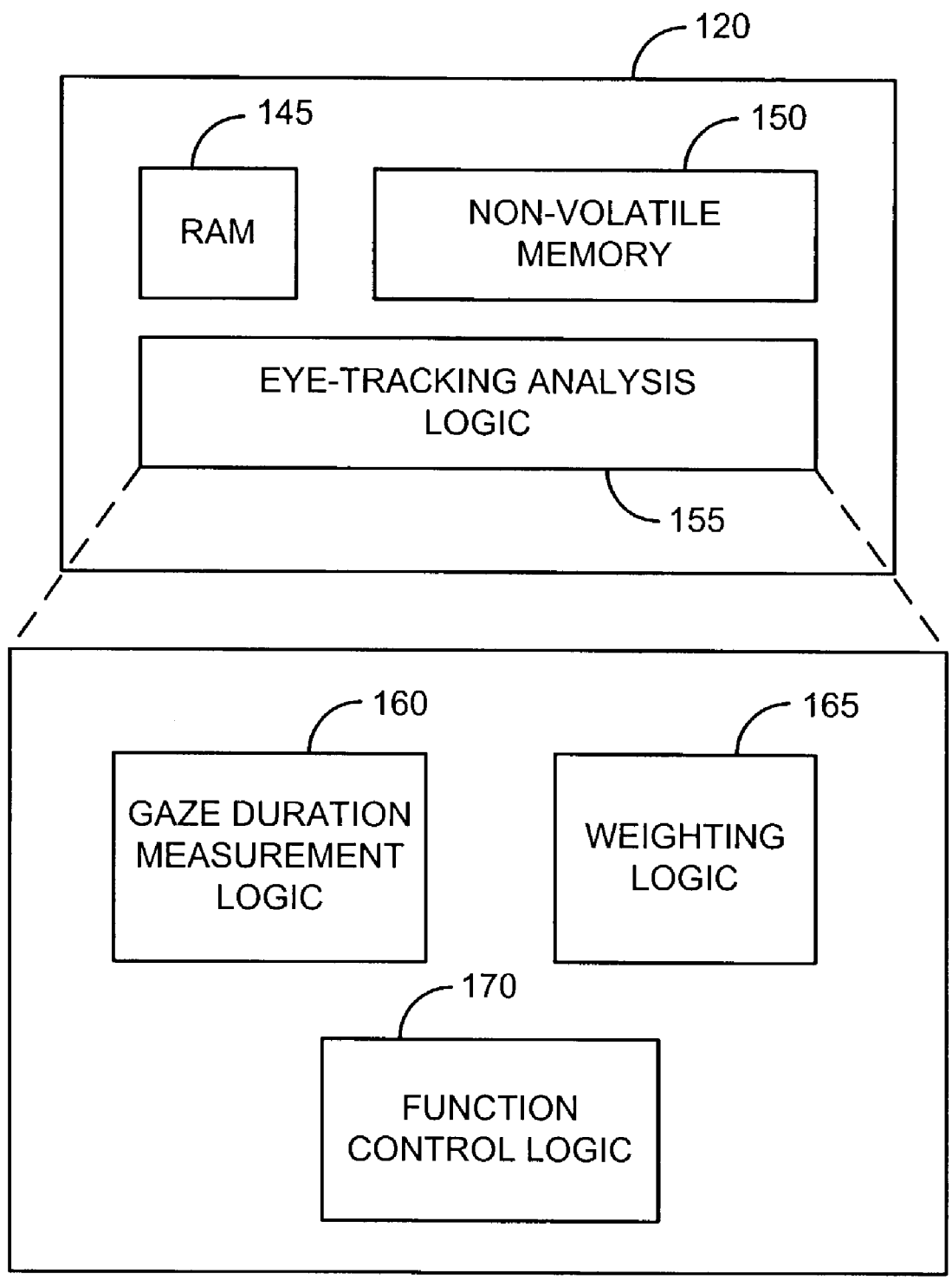
FIG. 1B is a diagram of a memory in the digital imaging device shown in FIG. 1A in accordance with an illustrative embodiment of the invention.

FIG. 1B is a diagram of memory 120 in accordance with an illustrative embodiment of the invention. Memory 120 may further comprise random access memory (RAM) 145, non-volatile memory 150, and eye-tracking analysis logic 155. Non-volatile memory 150 may, at least in part, be of the removable variety. Eye-tracking analysis logic 155 may comprise firmware or software instructions for execution by controller 105. In a different embodiment, eye-tracking analysis logic 155 may be implemented as custom hardware.

In general, eye-tracking analysis logic 155 analyzes the output of eye-tracking subsystem 130 and sets one or more functions or parameters in digital imaging device 100 accordingly. Eye-tracking analysis logic 155 may comprise gaze duration measurement logic 160, weighting logic 165, and function control logic 170. Gaze duration measurement logic 160 analyzes the trajectory of the user's gaze during the image composition process and, by relating that trajectory to a time reference, identifies locations within the scene on which the user's gaze lingers ("dwell locations"). A dwell location may, for example, be identified by a pair of coordinates identifying a specific point with the scene. Alternatively, a dwell location may be a somewhat larger sub-region of the scene bounded by a set of points defining a geometric figure. Weighting logic 165 applies a weighting algorithm to the identified dwell locations to determine an average location within the scene on which to base the setting of one or more functions in digital imaging device 100. Function control logic 170 may set one or more functions in digital imaging device 100 in accordance with the weighted dwell locations. In a different embodiment to be described in more detail later in this description, weighting logic 165 may be omitted because a single dwell location based on the instant at which S1 is pressed may be employed in setting parameters instead of multiple weighted dwell locations. In this embodiment, gaze duration measurement logic 160 may be configured to measure this single dwell location (direction of gaze at the time S1 is activated).

Eye-tracking subsystem 130 may be implemented using techniques that are well known in the related art. Eye-tracking subsystem 130 may, for example, illuminate the user's eye using an infrared (IR) source. Lenses and mirrors may be used to focus and direct an optical IR image reflected from the user's eye onto a photosensor (e.g., a CCD sensor array). By analyzing the position of the cornea, pupil, or retina in the resulting IR image, the direction in which the user is gazing may be determined. That measured direction of gaze may then be related to a particular portion of a scene at which the user is gazing during an image composition process. Eye-tracking systems typically require a calibration procedure during which specific characteristics of a particular user's eye is stored for future reference.

Eye-tracking control for autofocus in prior-art cameras typically operates in one of two modes. In a "one-shot" mode, eye-tracking subsystem 130 detects the direction of the user's gaze at the instant the user activates S1. In an alternative "servo" mode, eye-tracking may be performed continually throughout the image composition process. Some single-lens-reflex (SLR) film cameras produced by Canon have included sophisticated eye-tracking control of autofocus that, in a servo mode, may operate throughout the image composition process. This technology is described in detail in, for example, U.S. Pat. No. 6,035,054, the disclosure of which is incorporated herein by reference.

Figure 2A:
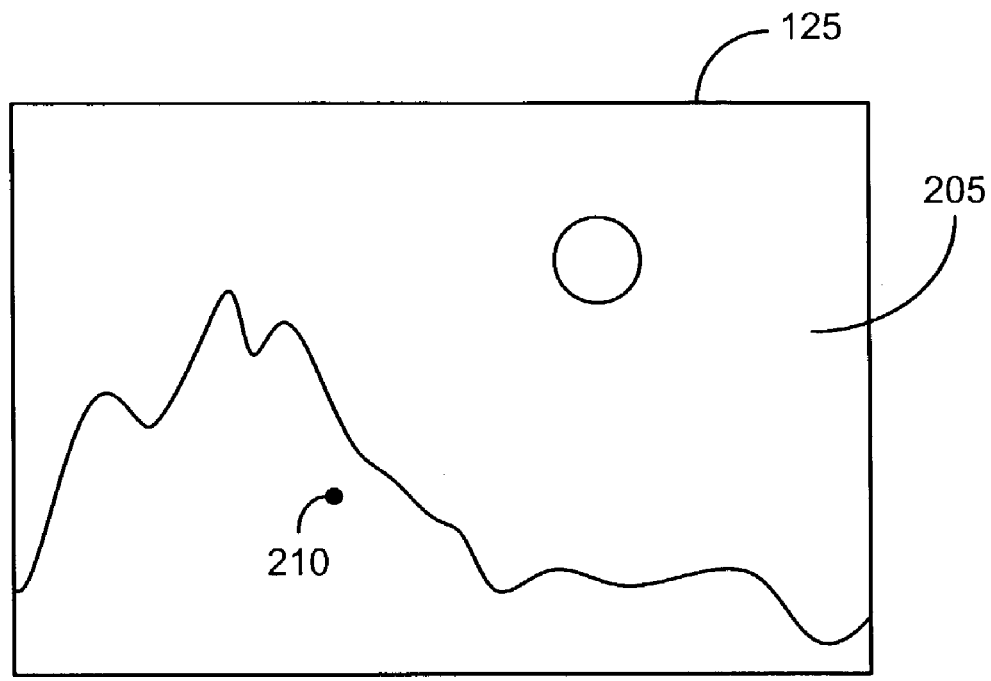
FIG. 2A is an illustration of a single dwell location at which a user's gaze is directed in accordance with an illustrative embodiment of the invention.
Figure 2B:
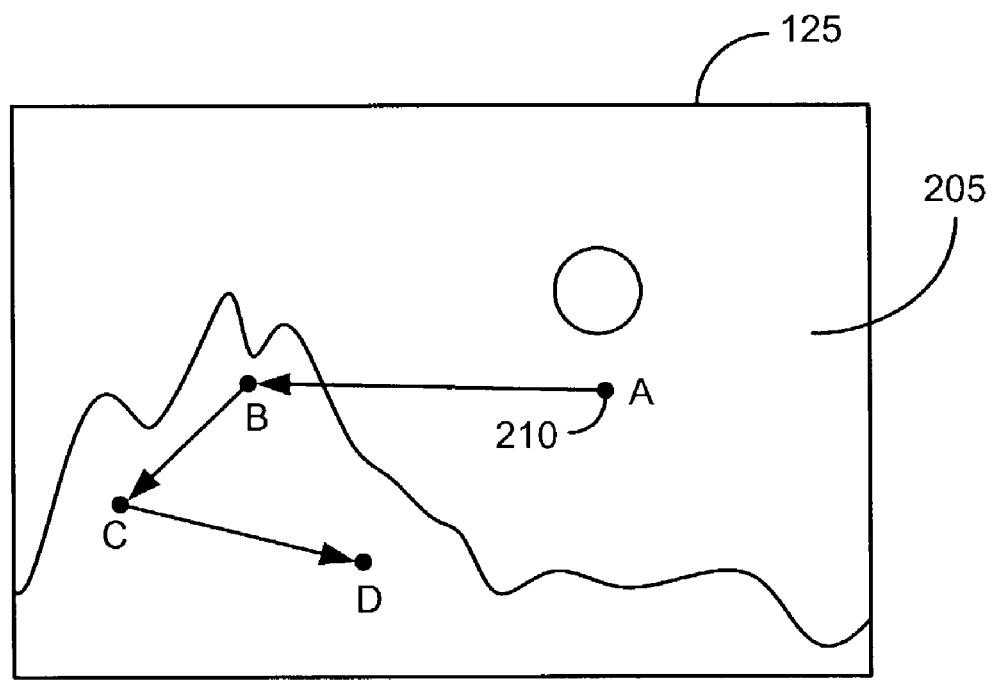
FIG. 2B is an illustration of a sequence of dwell locations on which a user's gaze lingers within a scene during an image composition process in accordance with another illustrative embodiment of the invention.

FIGS. 2A and 2B illustrate examples of using a single and multiple dwell locations, respectively, in accordance with an illustrative embodiment of the invention. In both figures, a scene 205 is shown within display 125 of digital imaging device 100. In FIG. 2A, a single dwell location 210 is identified at the moment S1 is activated. Functions such as autofocus, auto exposure, and auto color balance may be adjusted in digital imaging device 100 according to the characteristics (e.g., distance or color) of the scene at dwell location 210. In FIG. 2B, gaze duration measurement logic 160 has identified a series of four dwell locations 210 labeled A-D, A being the least recent and D being the most recent. Gaze duration measurement logic 160 may identify such dwell locations, for example, by noting any location within the scene for which its associated dwell time exceeds a threshold. This sequence of dwell locations 210 may be weighted in a variety of ways to identify a portion of the scene 205 on which to base the setting of functions in digital imaging device 100. For example, in one embodiment the most recent dwell location may be used to the exclusion of all others. Alternatively, multiple dwell locations may be weighted linearly or non-linearly to produce a weighted location within scene 205. A wide variety of mathematical expressions may be devised in which, for example, the recency and/or dwell time of a dwell location are scaled and summed to produce a weighted location within scene 205 on which the setting of one or more functions in digital imaging device 100 may be based. In one embodiment, the most recent dwell locations having the longest dwell times are weighted more heavily than other dwell locations not satisfying those criteria.

Once a single dwell location 210 or a weighted location has been determined, autofocus may be optimized in the usual manner based on the distance of that portion of scene 205 from digital imaging device 100. In the case of auto exposure, the exposure setting of digital imaging device 100 may be optimized based on a region surrounding a single dwell location 210 or a weighted location. The same is true for auto color balance. For example, a user who desires to emphasize a certain shadow in a scene may gaze at that portion of scene 205 to establish the shadow as a dwell location 210 (or a dominant dwell location in the case of weighted dwell locations). Auto exposure and/or color balance settings may then be optimized to favor the shadow. By providing the user with a preview of scene 205 as it would appear in a captured digital image, the user may see immediately how the shadow will be rendered in the final captured image. The result is that the shadow improves before the user's eyes as the image is being composed.

Figure 3:
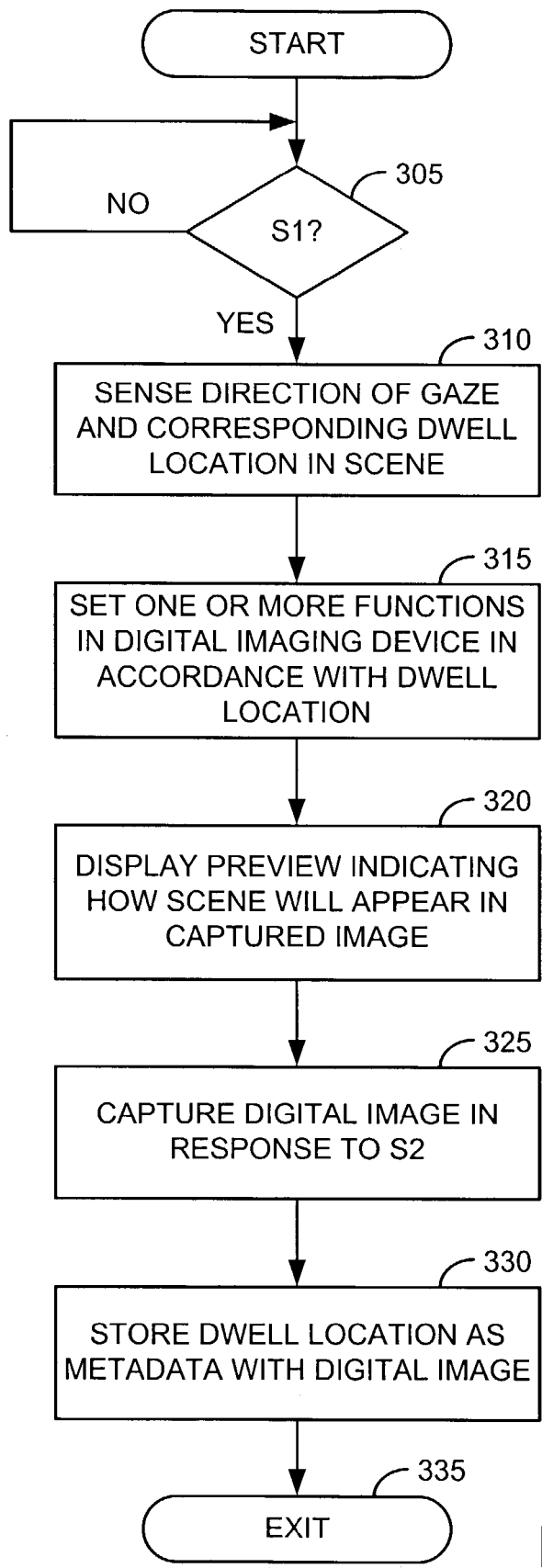
FIG. 3 is a flowchart of the operation of the digital imaging device shown in FIGS. 1A and 1B in accordance with an illustrative embodiment of the invention.

FIG. 3 is a flowchart of the operation of digital imaging device 100 in accordance with an illustrative embodiment of the invention. At 305, activation of S1 causes control to proceed to 310, where a single direction of gaze at the time S1 is activated is measured by gaze duration measurement logic 160. This is the single-shot eye-tracking control discussed above. The measured direction of gaze may be related through an analysis of angles to scene 205 to identify a single dwell location 210. At 315, one or more functions (e.g., autofocus, auto exposure, or auto color balance) may be set by function control logic 170 in accordance with the measured dwell location 210. Optionally, at 320, a preview of how scene 205 will appear in a captured digital image may be shown on display 125. In response to S2, a digital image may be captured at 325. Optionally, the dwell location 210 associated with the digital image may be stored with the digital image as metadata at 330. For example, the metadata may occupy a portion of a header in a Joint Photographic Experts Group (JPEG) file. The process then terminates at 335.

Figure 4:
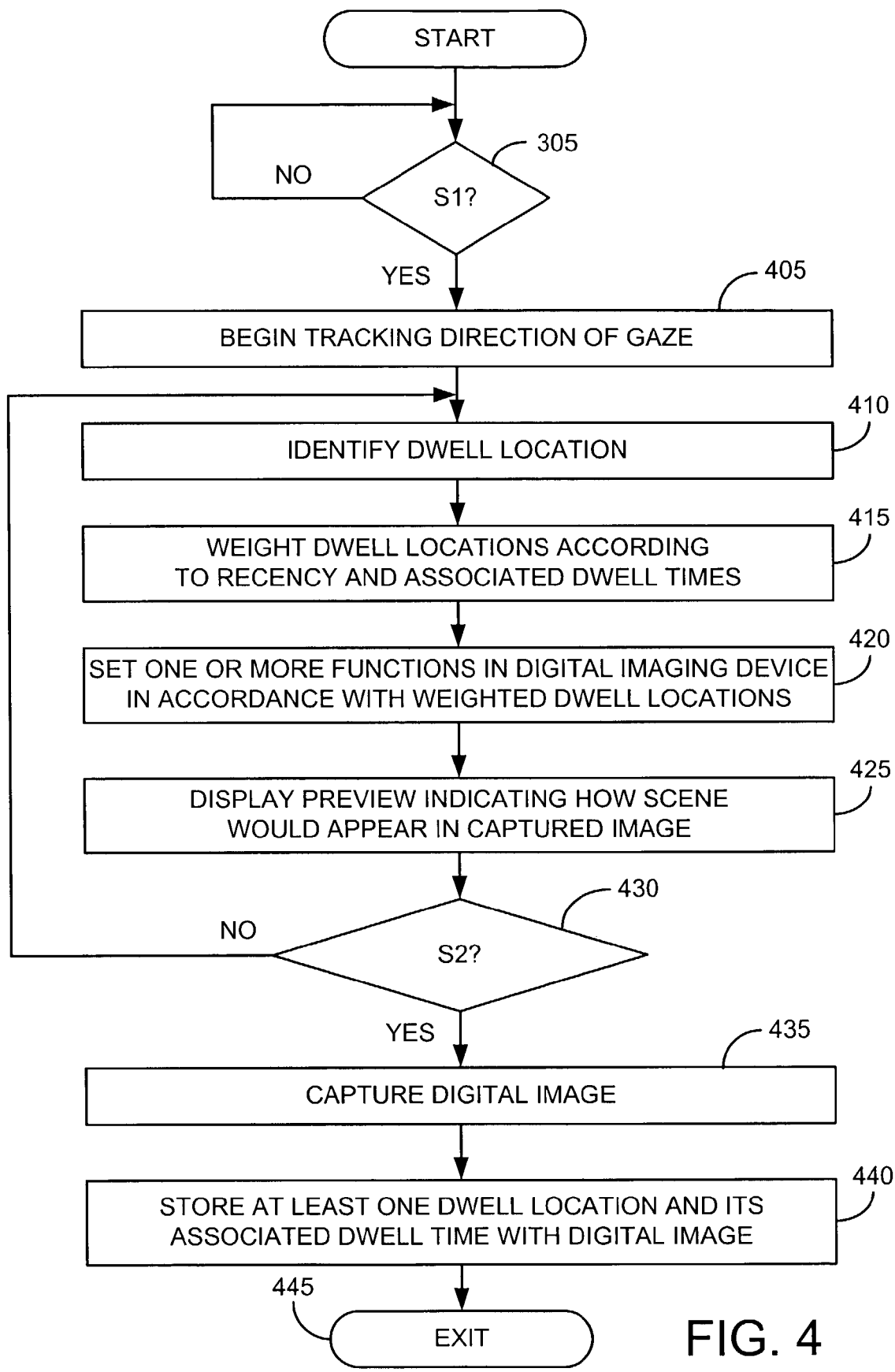
FIG. 4 is a flowchart of the operation of the digital imaging device shown in FIGS. 1A and 1B in accordance with another illustrative embodiment of the invention.

FIG. 4 is a flowchart of the operation of digital imaging device 100 in accordance with another illustrative embodiment of the invention. In response to S1 at 305, eye-tracking subsystem 130 begins tracking the user's direction of gaze throughout the image composition process at 405. At 410, gaze duration measurement logic 160 analyzes the output of eye-tracking subsystem 130 to identify dwell locations 210. Weighting logic 165 processes the dwell locations 210 identified thus far at 415. At 420, one or more functions in digital imaging device 100 such as autofocus, auto exposure, or auto color balance may be adjusted by function control logic 170 in accordance with the weighted dwell locations 210. At 425, a preview of scene 205 as it would appear in a captured digital image may be shown on display 125. In response to S2 at 430, a digital image may be captured at 435. At 440, at least one dwell location and its associated dwell time may be stored with the captured digital image as metadata. This embodiment optionally allows a rich history of the user's gaze pattern to be stored with the associated digital image. The process then terminates at 445.

Figure 5:
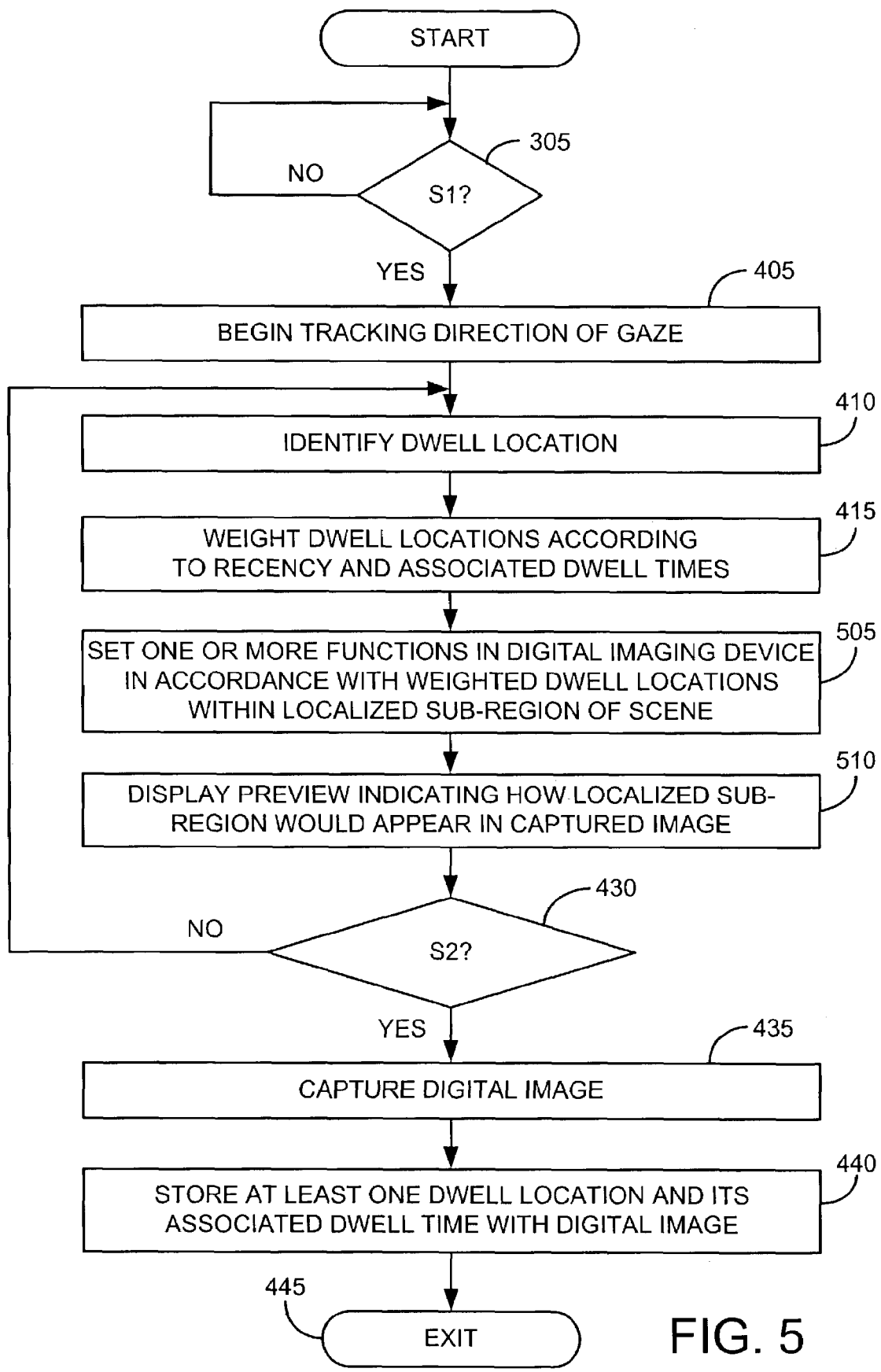
FIG. 5 is a flowchart of the operation of the digital imaging device shown in FIGS. 1A and 1B in accordance with yet another illustrative embodiment of the invention.

FIG. 5 is a flowchart of the operation of digital imaging device 100 in accordance with yet another illustrative embodiment of the invention. The process shown in FIG. 5 is similar to that in FIG. 4, except that, at 505, the setting of one or more functions in digital imaging device 100 by function control logic 170 is applied to a localized sub-region of scene 205 instead of the entire scene 205. For example, adjustment of color balance may be limited to the sky within a scene 205 to improve the appearance of clouds without affecting color balance elsewhere in the captured digital image. Such a mode in digital imaging device 100 may be activated automatically, by prior selection via a menu, or by interactive user control during composition using input controls 135. At 510, a preview may be shown on display 125 indicating how the localized sub-region would appear in a captured digital image.

In yet another illustrative embodiment of the invention, functions such as autofocus in digital imaging device 100 are not set based on dwell locations 210. Rather, one or more dwell locations 210 are simply identified and stored as metadata with the corresponding digital image captured by digital imaging device 100. Optionally, the measured dwell times associated with the dwell locations 210 may be included with the stored metadata.

Figure 6:
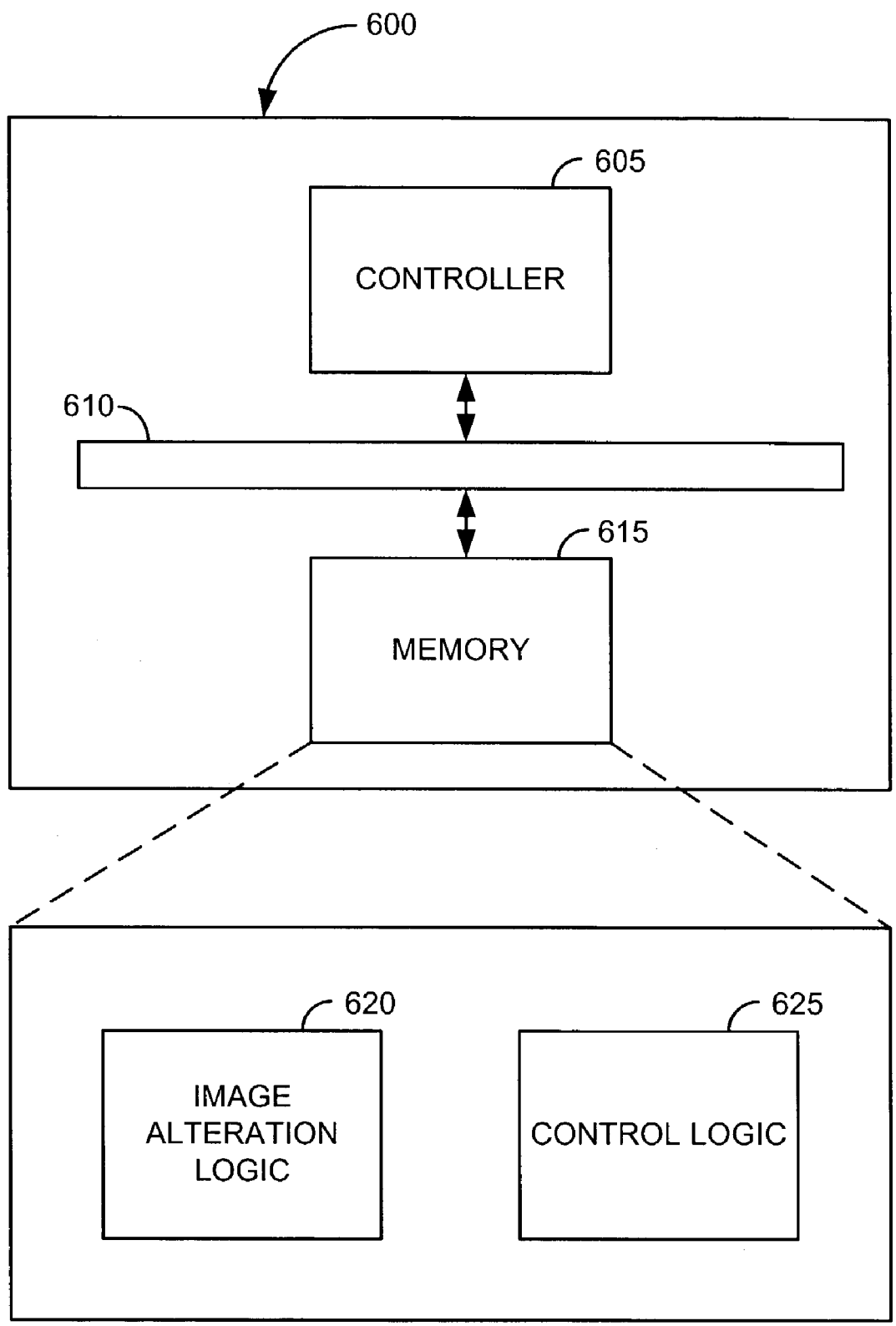
FIG. 6 is a functional block diagram of a digital image processing apparatus for post-processing digital images having accompanying metadata in accordance with an illustrative embodiment of the invention.

FIG. 6 is a functional block diagram of a digital image processing apparatus 600 for post-processing digital images having accompanying metadata in accordance with an illustrative embodiment of the invention. Digital image processing apparatus 600 may comprise, for example, a desktop personal computer (PC), notebook computer, digital camera, personal digital assistant (PDA), or any similar device capable of storing and processing digital images. In FIG. 6, controller 605 communicates over data bus 610 with memory 615. Memory 615 may further comprise image alteration logic 620 and control logic 625. These components may be implemented, for example, as software or firmware program instructions for execution on controller 605. In other embodiments, the functions provided by controller 605, memory 615, image alteration logic 620, and control logic 625 may instead be implemented in custom hardware. Image alteration logic 620 is configured to perform various alterations on digital images. Examples include cropping, correcting exposure, correcting color balance, and correcting tone reproduction. The functions of image alteration logic 620 may, for example, be embodied in an image editing application running on a PC. Control logic 625 interprets metadata such as that described above (a single dwell location or multiple dwell locations with their associated dwell times) and automatically applies the functions of image alteration logic 620 to a digital image stored in memory 615. Thus, the metadata stored with the digital image facilitates automatic post-processing of the image according to the portions of the image that are of greatest importance to the user without the need for user involvement.

Figure 7A:
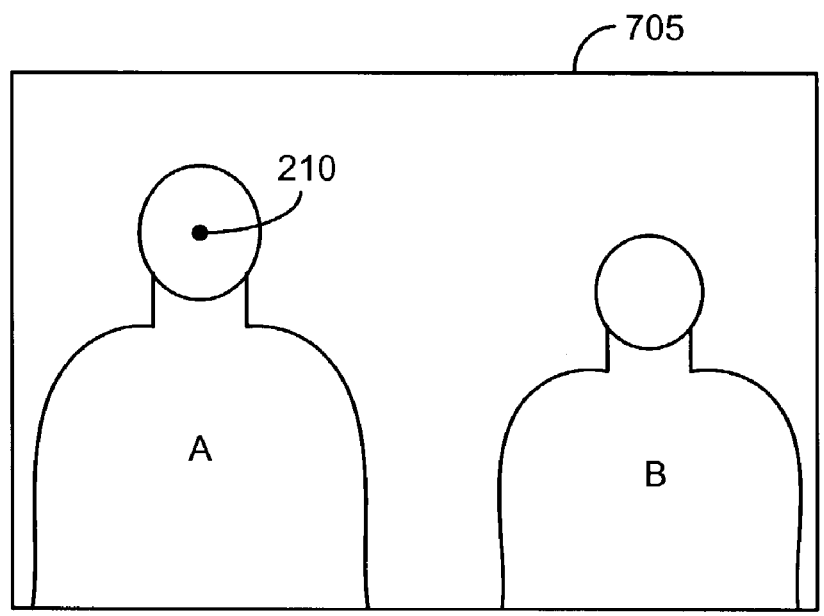
FIG. 7A is an illustration of a digital image with which a single dwell location has been stored in accordance with an illustrative embodiment of the invention.
Figure 7B:
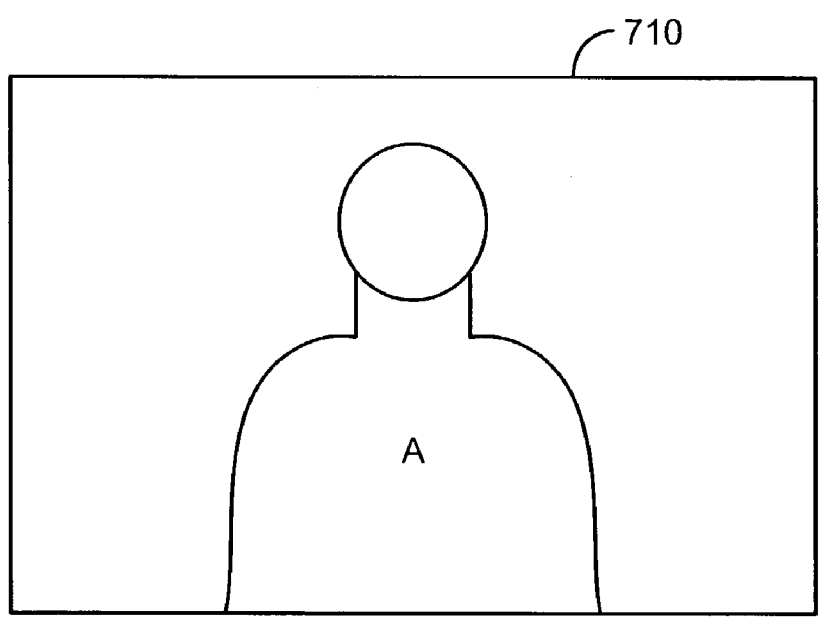
FIG. 7B is an illustration of the digital image shown in FIG. 7A after having been cropped automatically based on the dwell location stored with the digital image in accordance with an illustrative embodiment of the invention.
Figure 7C:
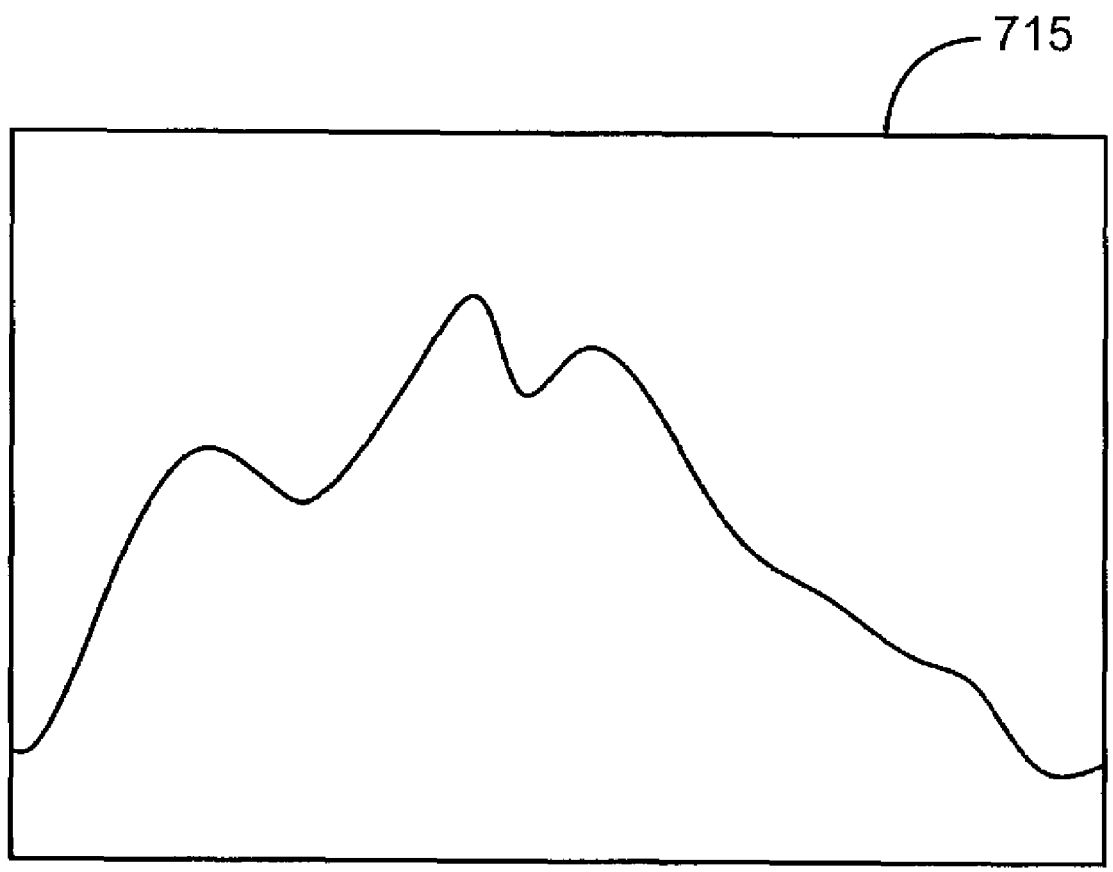
FIG. 7C is an illustration of a digital image corresponding to the scene shown in FIG. 2B after it has been cropped automatically based on a weighting of the dwell locations shown in FIG. 2B in accordance with another illustrative embodiment of the invention.

FIG. 7A is an illustration of a digital image 705 with which a single dwell location 210 (e.g., coordinates within digital image 705) has been stored in accordance with an illustrative embodiment of the invention. Digital image 705 includes two personages labeled A and B. The dwell location 210 stored with digital image 705 is centered on personage A's face, indicating that the photographer may have been more interested in personage A than in personage B when digital image 705 was captured. After automatic post-processing by control logic 625 and image alteration logic 620, the cropped digital image 710 shown in FIG. 7B may be produced. The cropping algorithm of image alteration logic 620 may be configured according to a variety of rules such as the "rule of thirds" that are well known in the photographic art. Applying more sophisticated rules (as opposed to simply placing the dwell location at the exact center of the cropped image 710) results in a more aesthetically pleasing, professional-looking cropped image 710. Automatic post-processing based on a single stored dwell location may also be applied to automatic exposure correction or automatic correction of tone reproduction.

Where a rich gaze-direction history comprising multiple dwell locations 210 and their associated dwell times has been stored with the digital image, digital image processing apparatus 600 may perform more complex automated cropping, correction of exposure, or correction of tone reproduction. For example, a digital image produced from scene 205 in FIG. 2B, including as metadata the four associated dwell locations 210A-D and their associated dwell times, may be cropped automatically to produce an image such as that shown in FIG. 7C. Control logic 625 may produce the image in FIG. 7C based, for example, on dwell locations 210B, C, and D in FIG. 2B being more recent than A and, in this example, having dwell times that are assumed to be longer. Alternatively, one or more automatically post-processed images may be presented to the user, optionally accompanied by the original unmodified image, and the user may select a preferred automatically altered image. In this embodiment, the various automatically post-processed images may be based on different assumptions about the user's intent derived from dwell locations 210 and their associated chronology and dwell times.

Figure 8:
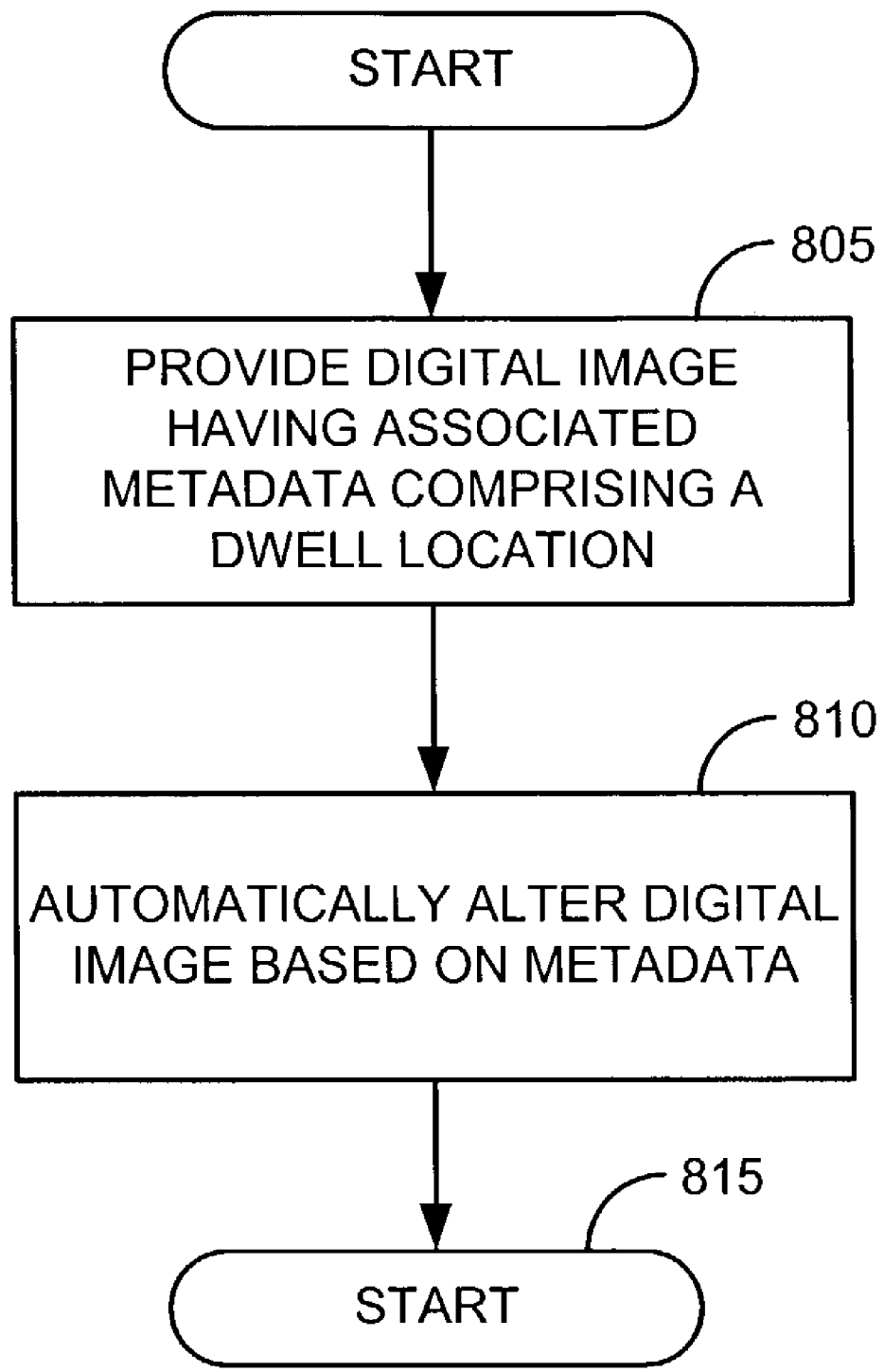
FIG. 8 is a flowchart of the operation of the digital image processing apparatus shown in FIG. 6 in accordance with an illustrative embodiment of the invention.

FIG. 8 is a flowchart of the operation of the digital image processing apparatus 600 shown in FIG. 6 in accordance with an illustrative embodiment of the invention. At 805, a digital image is providing with which metadata comprising a single dwell location 210 has been stored as explained above. At 810, control logic 625 interprets the dwell location 210 and automatically applies one or more functions of image alteration logic 620 to produce an altered digital image. The process terminates at 815.

Figure 9:
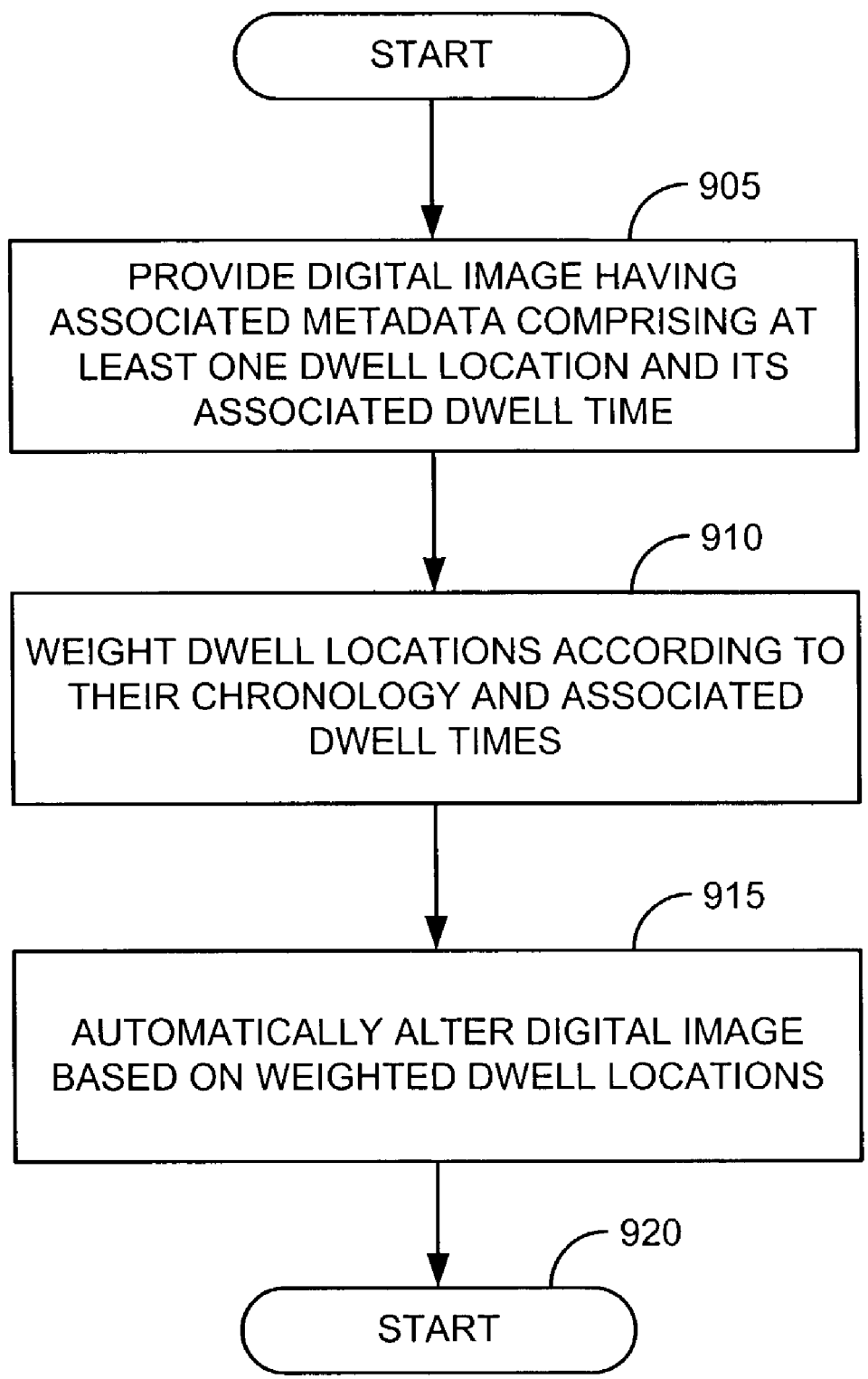
FIG. 9 is a flowchart of the operation of the digital image processing apparatus shown in FIG. 6 in accordance with another illustrative embodiment of the invention.

FIG. 9 is a flowchart of the operation of the digital image processing apparatus 600 shown in FIG. 6 in accordance with another illustrative embodiment of the invention. At 905, a digital image is provided with which metadata comprising at least one dwell location 210 and its associated dwell time has been stored. At 910, control logic 625 interprets and weights the dwell locations 210. For example, control logic 625 may weight the dwell locations 210 according to their chronology (where each occurred in the sequence) and their associated dwell times. Control logic 625 may then, at 915, automatically apply one or more functions of image alteration logic 620 to the digital image to produce an altered digital image. The process then terminates at 920.

The foregoing description of the present invention has been presented for the purposes of illustration and description. It is not intended to be exhaustive or to limit the invention to the precise form disclosed, and other modifications and variations may be possible in light of the above teachings. The embodiments were chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method for controlling the operation of a digital imaging device, comprising:
   tracking, throughout a digital image composition process, a direction of gaze of a user viewing a scene through the digital imaging device;
   identifying at least one dwell location comprising a portion of the scene on which the direction of gaze lingers;
   weighting the at least one dwell locations; and
   setting at least one function in the digital imaging device in accordance with the weighted dwell locations wherein setting at least one function in the digital imaging device in accordance with the weighted dwell locations is applied to a localized sub-region of the scene.

2. The method of claim 1, further comprising:
   displaying, in response to setting at least one function in the digital imaging device in accordance with the weighted dwell locations, a preview indicating how the scene would appear in a digital image captured by the digital imaging device.

3. The method of claim 1, further comprising:
   capturing a digital image in the digital imaging device; and
   storing with the digital image as metadata at least one dwell location.

4. The method of claim 3, wherein the metadata stored with the digital image further comprises an associated dwell time for each stored dwell location.

5. The method of claim 1, wherein the dwell locations are weighted according to their recency.

6. The method of claim 1, wherein each dwell location has an associated dwell time and the dwell locations are weighted according to their associated dwell times.

7. The method of claim 6, wherein more recent dwell locations having longer dwell times are weighted more heavily than other dwell locations.

8. The method of claim 1, wherein the at least one function comprises at least one of focus, exposure, and color balance.

9. The method of claim 1, further comprising:
   displaying a preview of the localized sub-region indicating how that localized sub-region would appear in a digital image captured by the digital imaging device.

10. A digital imaging device, comprising:
    an eye-tracking subsystem to track, throughout a digital image composition process, a direction of gaze of a user viewing a scene through the digital imaging device;
    gaze duration measurement logic to analyze the output of the eye-tracking subsystem and identify at least one dwell location comprising a portion of the scene on which the direction of gaze lingers;
    weighting logic configured to weight the at least one dwell locations; and
    control logic configured to set at least one function in the digital imaging device in accordance with the weighted dwell locations wherein the control logic is configured to set the at least one function in the digital imaging device in accordance with the weighted dwell locations within a localized sub-region of the scene.

11. The digital imaging device of claim 10, wherein the gaze duration measurement logic is further configured to measure an associated dwell time for each dwell location.

12. The digital imaging device of claim 10, further comprising:
    a display on which to show, in response to the control logic setting at least one function in the digital imaging device in accordance with the weighted dwell locations, a preview indicating how the scene would appear in a digital image captured by the digital imaging device.

13. The digital imaging device of claim 10, further comprising:
    an imaging module to capture a digital image; and
    a memory in which to store as metadata with the digital image at least one dwell location.

14. The digital imaging device of claim 13, wherein the metadata stored with the digital image further comprises an associated dwell time for each stored dwell location.

15. The digital imaging device of claim 10, further comprising:
    a display on which to show, in response to the control logic setting at least one function in the digital imaging device in accordance with the weighted dwell locations within the localized sub-region, a preview indicating how that localized sub-region would appear in a digital image captured by the digital imaging device.

16. The digital imaging device of claim 10, wherein the at least one function comprises at least one of focus, exposure, and color balance.

17. A digital imaging device, comprising:
an eye-tracking subsystem to detect a direction of gaze of a user viewing a scene through the digital imaging device, the direction of gaze corresponding to a dwell location comprising a particular portion of the scene;
control logic configured to set at least one function in the digital imaging device in accordance with the dwell location and is applied to a localized sub-region of the scene;
an imaging module to capture a digital image; and
a memory in which to store the dwell location as metadata with the digital image.

18. The digital imaging device of claim 17, further comprising:
a display on which to show, in response to the control logic setting at least one function in the digital imaging device in accordance with the dwell location, a preview indicating how the scene would appear in a digital image captured by the digital imaging device.

19. The digital imaging device of claim 17, wherein the at least one function comprises at least one of focus, exposure, and color balance.

20. A digital imaging device, comprising:
tacking means for tracking, throughout a digital image composition process, a direction of gaze of a user viewing a scene through the digital imaging device;
means for analyzing the output of the tracking means to identify at least one dwell location comprising a portion of the scene on which the direction of gaze lingers, the means for analyzing the output of the tracking means being configured to measure an associated dwell time for each dwell location;
means for weighting the at least one dwell locations; and
means for setting at least one function in the digital imaging device in accordance with the weighted dwell locations wherein setting at least one function in the digital imaging device in accordance with the weighted dwell locations is applied to a localized sub-region of the scene.

21. The digital imaging device of claim 20, further comprising:
means for capturing a digital image; and
means for storing as metadata with the digital image at least one dwell location and its associated dwell time.

22. A digital imaging device, comprising:
means for detecting a direction of gaze of a user viewing a scene through the digital imaging device, the direction of gaze corresponding to a dwell location comprising a particular portion of the scene;
means for setting at least one function in the digital imaging device in accordance with the dwell location wherein setting at least one function in the digital imaging device in accordance with the dwell locations is applied to a localized sub-region of the scene;
means for capturing a digital image; and
means for storing the digital image with the dwell location.

* * * * *

UNITED STATES PATENT AND TRADEMARK OFFICE
CERTIFICATE OF CORRECTION

PATENT NO.        : 7,259,785 B2                                Page 1 of 1
APPLICATION NO.   : 10/425292
DATED             : August 21, 2007
INVENTOR(S)       : Donald J. Stavely et al.

It is certified that error appears in the above-identified patent and that said Letters Patent is hereby corrected as shown below:

In column 9, line 27, in Claim 20, delete "tacking" and insert -- tracking --, therefor.

Signed and Sealed this

Fifth Day of May, 2009

JOHN DOLL
*Acting Director of the United States Patent and Trademark Office*